US010448986B2

(12) United States Patent
Zikorus et al.

(10) Patent No.: US 10,448,986 B2
(45) Date of Patent: Oct. 22, 2019

(54) ELECTROSURGICAL MEDICAL DEVICE WITH POWER MODULATION

(71) Applicant: Covidien LP, Mansfield, MA (US)

(72) Inventors: Arthur W. Zikorus, San Jose, CA (US); Michael S. Mirizzi, San Jose, CA (US)

(73) Assignee: Covidien LP, Mansfield, MA (US)

(*) Notice: Subject to any disclaimer, the term of this patent is extended or adjusted under 35 U.S.C. 154(b) by 627 days.

(21) Appl. No.: 14/038,827

(22) Filed: Sep. 27, 2013

(65) Prior Publication Data

US 2015/0094703 A1    Apr. 2, 2015

(51) Int. Cl.
| | |
|---|---|
| *A61B 18/10* | (2006.01) |
| *A61B 18/04* | (2006.01) |
| *A61B 18/12* | (2006.01) |
| *A61B 90/00* | (2016.01) |
| *A61B 18/14* | (2006.01) |
| *A61B 18/00* | (2006.01) |

(52) U.S. Cl.
CPC .............. *A61B 18/04* (2013.01); *A61B 18/10* (2013.01); *A61B 18/1206* (2013.01); *A61B 90/08* (2016.02); *A61B 18/1492* (2013.01); *A61B 2018/0063* (2013.01); *A61B 2018/00136* (2013.01); *A61B 2018/00404* (2013.01); *A61B 2018/00642* (2013.01); *A61B 2018/00726* (2013.01); *A61B 2018/00791* (2013.01); *A61B 2018/1226* (2013.01)

(58) Field of Classification Search
CPC ........ A61B 2018/1226; A61B 18/1206; A61B 2018/1266; A61B 18/10
See application file for complete search history.

(56) References Cited

U.S. PATENT DOCUMENTS 4,196,734 A * 4/1980 Harris ................ A61B 18/1206
  219/233
4,835,410 A * 5/1989 Bhagwat .................. B25F 5/00
  307/64

(Continued)

FOREIGN PATENT DOCUMENTS

| CN | 1296014 C | 1/2007 |
| CN | 100998500 A | 7/2007 |

(Continued)

OTHER PUBLICATIONS

Notice of Reasons for Rejection, and translation thereof, from counterpart Japanese Application No. 2014-196441, dated Aug. 19, 2015, 9 pp.

(Continued)

*Primary Examiner* — Jaymi E Della
(74) *Attorney, Agent, or Firm* — Shumaker & Sieffert, P.A.

(57) ABSTRACT

An electrosurgical ablation device provides pulse width modulated DC power to a heating segment in a catheter for use in providing treatment. In some embodiments the DC power to be modulated is sourced from an AC/DC power converter coupled to a source of AC power. In some embodiments the DC power to be modulated is sourced from a battery. In some embodiments the device switchably selects for modulation DC power sourced from either the AC/DC power converter or the battery, for example based on availability of power from the AC/DC power converter.

24 Claims, 8 Drawing Sheets

(56) References Cited

U.S. PATENT DOCUMENTS

| | | | |
|---|---|---|---|
| 4,869,248 A * | 9/1989 | Narula | A61B 18/082 606/29 |
| 5,246,438 A * | 9/1993 | Langberg | A61B 18/08 600/374 |
| 5,409,008 A * | 4/1995 | Svenson | A61B 18/1492 600/374 |
| 5,484,400 A * | 1/1996 | Edwards | A61B 18/00 604/22 |
| 5,517,989 A * | 5/1996 | Frisbie | A61B 5/0422 600/454 |
| 5,836,943 A * | 11/1998 | Miller, III | A61B 18/1206 606/34 |
| 5,971,980 A * | 10/1999 | Sherman | A61B 17/22012 606/34 |
| 6,012,457 A * | 1/2000 | Lesh | A61B 18/10 128/898 |
| 6,070,590 A * | 6/2000 | Hoffmann | A61N 1/3956 128/898 |
| 6,123,084 A * | 9/2000 | Jandak | A61B 18/08 128/898 |
| 7,196,911 B2 * | 3/2007 | Takano | H02J 7/022 320/114 |
| 7,513,896 B2 | 4/2009 | Orszulak | |
| 7,875,025 B2 | 1/2011 | Cockburn et al. | |
| 8,349,174 B2 * | 1/2013 | Bedingfield | A61M 1/16 210/134 |
| 9,121,774 B2 * | 9/2015 | Brannan | A61B 18/1815 |
| 2002/0161361 A1 * | 10/2002 | Sherman | A61B 18/02 606/21 |
| 2003/0125720 A1 | 7/2003 | Woodard et al. | |
| 2004/0006337 A1 * | 1/2004 | Nasab | A61B 18/1206 606/41 |
| 2004/0082946 A1 * | 4/2004 | Malis | A61B 18/1206 606/34 |
| 2005/0010206 A1 | 1/2005 | Nasab et al. | |
| 2005/0182393 A1 | 8/2005 | Abboud et al. | |
| 2005/0222623 A1 * | 10/2005 | Kroll | A61N 1/326 607/2 |
| 2006/0217706 A1 * | 9/2006 | Lau | A61B 17/29 606/45 |
| 2008/0119841 A1 * | 5/2008 | Geisel | A61B 18/10 606/29 |
| 2008/0281391 A1 * | 11/2008 | MacAdam | A61B 5/042 607/122 |
| 2009/0043365 A1 * | 2/2009 | Friedland | A61H 1/008 607/108 |
| 2009/0076496 A1 | 3/2009 | Azure | |
| 2009/0084771 A1 | 4/2009 | Nomura | |
| 2009/0171343 A1 | 7/2009 | Paul et al. | |
| 2010/0022937 A1 * | 1/2010 | Bedingfield | A61M 1/16 604/6.09 |
| 2010/0228246 A1 | 9/2010 | Marion | |
| 2011/0166563 A1 | 7/2011 | Cheng et al. | |
| 2011/0224663 A1 | 9/2011 | Heim et al. | |
| 2011/0288543 A1 * | 11/2011 | Cheng | A61B 18/1233 606/41 |
| 2012/0041436 A1 * | 2/2012 | Ullrich | A61B 18/12 606/39 |
| 2012/0059286 A1 * | 3/2012 | Hastings | A61N 7/022 601/2 |
| 2012/0101434 A1 | 4/2012 | Stewart et al. | |
| 2012/0143099 A1 | 6/2012 | Daniels et al. | |
| 2012/0165806 A1 | 6/2012 | Brannan | |
| 2012/0179155 A1 | 7/2012 | Strul et al. | |
| 2012/0191085 A1 * | 7/2012 | Eckhouse | A45D 26/0028 606/33 |
| 2012/0310229 A1 * | 12/2012 | Gregg | A61B 18/1445 606/33 |
| 2013/0041436 A1 * | 2/2013 | Ruse | A61B 18/1477 607/99 |
| 2013/0066311 A1 * | 3/2013 | Smith | H02H 3/08 606/33 |
| 2013/0186828 A1 | 7/2013 | Bedingfield et al. | |
| 2014/0207124 A1 * | 7/2014 | Aldridge | A61B 17/00234 606/1 |

FOREIGN PATENT DOCUMENTS

| | | |
|---|---|---|
| CN | 101027009 A | 8/2007 |
| CN | 101156803 A | 4/2008 |
| CN | 102202591 A | 9/2011 |
| CN | 202666197 U | 1/2013 |
| EP | 1181895 A2 | 2/2002 |
| EP | 1723922 A1 | 11/2006 |
| EP | 2829248 A1 | 1/2015 |
| JP | S5876345 B2 | 9/1983 |
| JP | 63279833 A | 11/1988 |
| JP | H09306638 A | 11/1997 |
| JP | 2008534068 A | 8/2008 |
| JP | 200986963 A | 4/2009 |
| WO | 9320770 A2 | 10/1993 |
| WO | 2006104835 A1 | 10/2006 |
| WO | 2008141104 A2 | 11/2008 |
| WO | 2010042398 A1 | 4/2010 |
| WO | 2010051305 A1 | 5/2010 |
| WO | 2012033860 A1 | 3/2012 |
| WO | 2013090528 A1 | 6/2013 |
| WO | 2014181077 A1 | 11/2014 |

OTHER PUBLICATIONS

Notice of Preliminary Rejection, and translation thereof, from counterpart Korean Application No. 10-2014-128152, dated Aug. 26, 2015, 11 pp.

Extended Search Report from counterpart European Patent Application No. 14184088.4, dated Nov. 25, 2014, 7 pp.

First Office Action, and translation thereof, from counterpart Chinese Application No. 201410502631.3, dated Mar. 15, 2016, 16 pp.

Final Office Action, and translation thereof, from counterpart Japanese Patent Application No. 2014-196441, dated Mar. 8, 2016, 7 pp.

Final Office Action, and translation thereof, from counterpart Korean Patent Application No. 10-2014-0128152, dated Mar. 29, 2016, 5 pp.

Communication pursuant to Article 94(3) EPC from counterpart European Application No. 14184088.4, dated Mar. 31, 2017, 4 pp.

Second Office Action from counterpart Chinese Application No. 201410502631.3, dated Nov. 2, 2016, 9 pp.

Third Office Action, and translation thereof, from counterpart Chinese Application No. 201410502631.3, dated Apr. 5, 2017, 18 pp.

Examination Report from counterpart European Application No. 14184088.4, dated Feb. 27, 2018, 4 pp.

Notification to Grant Patent Right for Invention, and translation thereof, from counterpart Chinese Patent Application No. 201410502631.3, dated Sep. 30, 2017, 3 pp.

Intent to Grant dated Dec. 7, 2018, from counterpart European Application No. 14184088.4, 31 pp.

* cited by examiner

ELECTROSURGICAL MEDICAL DEVICE WITH POWER MODULATION

TECHNICAL FIELD

The present embodiments relate generally to medical treatment devices, and more particularly to electrosurgical devices with power modulation.

BACKGROUND OF THE INVENTION

Various medical procedures use a treatment device to apply energy to a body part of a patient. For example, techniques currently used for endovenous treatment for venous reflux disease, as well as other diseases in hollow anatomical structures (HAS), include electrosurgical procedures, including electrosurgical heating, radio frequency ablation (RFA), and laser ablation. These techniques generally involve a treatment apparatus or system that is configured to heat tissue at a treatment site within the HAS. For example, electrosurgical heating for treating venous reflux disease may use radio frequency current to apply energy to create targeted tissue ablation to seal off damaged veins. Electrosurgical equipment typically includes a generator, such as an RF generator, and a catheter having a heating segment located at the distal end, which is inserted into the vein(s) during treatment. The heating segment may use RF energy driven by the RF generator to heat and seal the vein. Electrosurgical treatments are also used in other medical treatments, such as, for example, arthroscopic surgery, renal denervation, and cardiac surgery.

Typically, electrosurgical procedures may be performed using devices powered by alternating current (AC) power sources. Unfortunately, AC power sources may not always be available or reliable in all locations.

BRIEF SUMMARY OF THE INVENTION

Aspects of the invention relate to electrosurgical devices, for example for use in medical treatments capable of utilizing AC and/or DC power, while providing appropriate power to the treatment device to provide effective and safe treatment. In general, in one aspect, an implementation of the disclosure features a direct current (DC) powered electrosurgical device including a catheter having a heating segment and modulation circuitry configured to modulate DC power provided to the heating segment. The electrosurgical device also includes at least one DC power source for providing the DC power to the first circuitry.

One or more of the following features maybe included. In some such aspects the modulation is pulse width modulation (PWM). In some such aspects the modulation circuitry includes pulse width modulation (PWM) driver circuitry and a switch. In some such aspects the at least one DC power source comprises two DC power sources. In some such aspects, a first of the two DC power sources comprises an AC/DC power converter and a second of the two DC power sources comprises a battery. Some such aspects further comprise a switch to switchably provide power from either the AC/DC converter or the battery to the PWM circuitry for provision to the heating segment. In some such aspects the AC/DC converter and the battery are coupled in parallel to the PWM circuitry. Some such aspects further comprise a DC/DC power converter coupled between the AC/DC power converter and the PWM circuitry. In some such aspects the heating segment comprises a resistive coil. In some such aspects the resistive coil is housed in a plastic cover. In some such aspects a frequency of the PWM is in a range of 1 kHz to 50 kHz, inclusive.

In general, in another aspect, the implementation of the disclosure features a method of operating an electrosurgical device, including providing direct current (DC) power, modulating the DC power using pulse width modulation (PWM), and applying the modulated DC power to a heating element in a catheter.

One or more of the following features may be included. In some aspects modulating the DC power using PWM includes providing the DC power to a switch, and opening and closing the switch using a PWM driver signal. In some such aspects a frequency of the PWM is in the range of 1 kHz to 50 kHz, inclusive. In some such aspects providing DC power includes selectably providing DC power from an AC/DC power converter or from a battery. In some such aspects selection of provision of DC power from the AC/DC power converter or from the battery is based on availability of AC power to the AC/DC power converter. In some such aspects selection of DC power from the AC/DC power converter or from the battery may be performed during application of power to the heating element.

In general, in still another aspect, the implementation of the disclosure features an electrosurgical device, including an AC/DC power converter and a battery. The device also includes a catheter including a resistive coil. Circuitry is included for switching provision of power to the resistive coil from power sourced from the AC/DC power converter to power sourced from the battery based on a cessation of availability of DC power from the AC/DC power converter.

One or more of the following features maybe included. Some aspects further include pulse width modulation (PWM) circuitry for modulating power provided to the resistive coil.

These and other aspects of the invention are more fully comprehended upon review of this disclosure.

DETAILED DESCRIPTION

The following discusses various embodiments with reference to the figures. Directional terms used herein, such as proximal, distal, upper, lower, clockwise, counterclockwise, etc., are generally used with reference to the configurations shown in the figures. For example, a component that is described as rotating clockwise when viewed from the perspectives shown in the figures may be said to rotate counterclockwise when viewed from the opposite perspective. Furthermore, the present embodiments may be modified by altering or reversing the positions or directions of movement of various components. Accordingly, directional terms used herein should not be interpreted as limiting.

Figure 1:
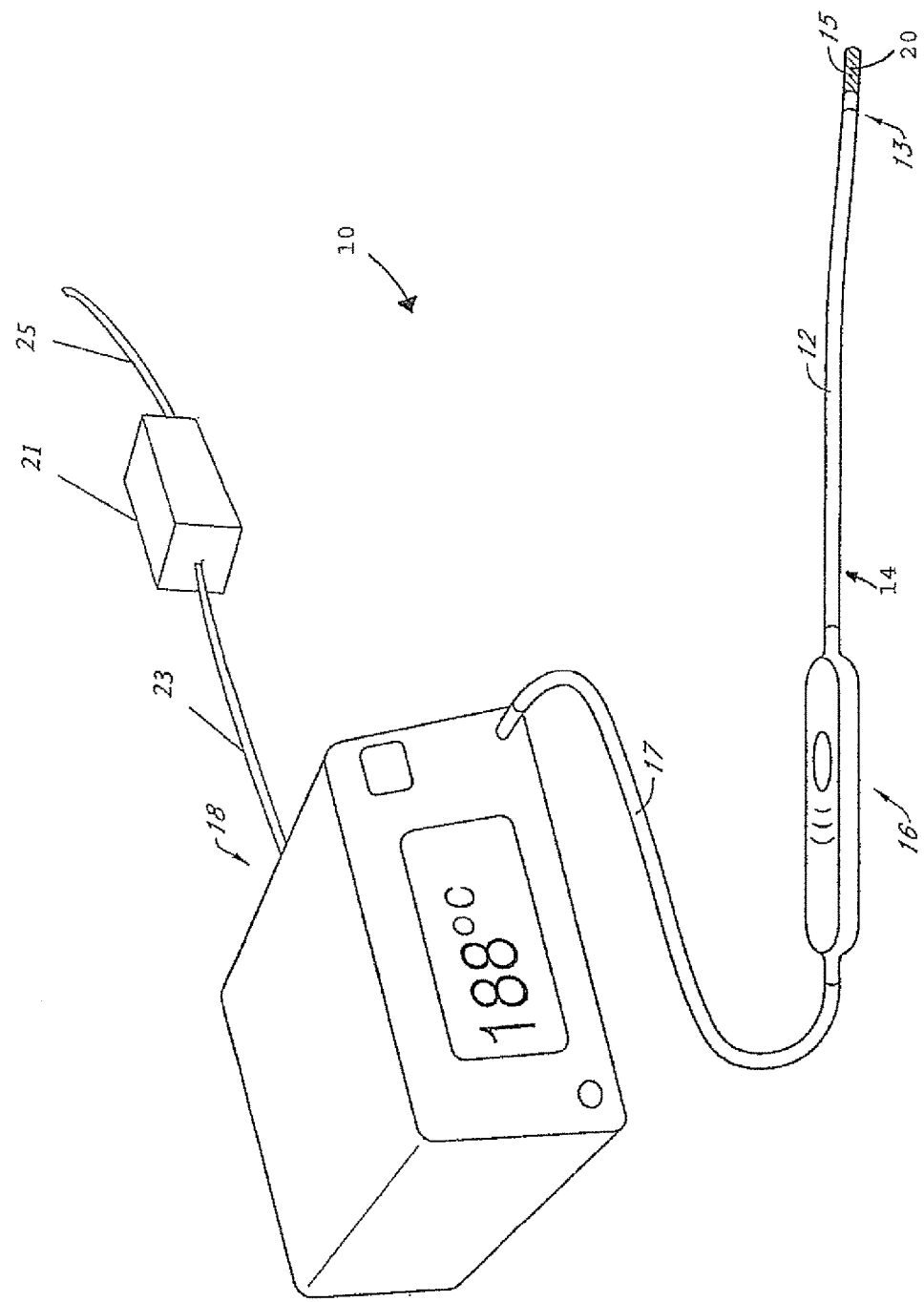
FIG. 1 illustrates a medical treatment system in accordance with aspects of the invention.

Referring to FIG. 1, an exemplary medical treatment 10 system may include a catheter shaft 12 having a distal end 13 and a proximal end 14. A heating segment 15 is operably attached towards or adjacent the distal end of the catheter shaft and a handle 16 is attached at the proximal end of the catheter shaft. A cable 17 electrically connects the heating segment 15 to a generator system 18. The cable 17 may be integral to the handle and removably connected to the generator system. Alternatively, the cable 17 may be removably connected to the handle.

The heating segment 15 includes a heating element 20. The heating element 20 may in some embodiments be a resistive coil, which may be driven, for example, by RF energy. Preferably, the relative resistance or impedance of the heating element 20 is designed to correlate to, or match, relative resistance or impedance of an output of the generator system 18 to which the heating element 20 is coupled. For example, the resistance of the heating element 20 may be determined by a wire gage that relates to the catheter diameter, the energy required during treatment, and/or the power source specifications. The heating element 20 may comprise a wide variety of conductive materials, such as, for example, nickel chromium (NICHROME®), a nickel iron alloy (for example Alloy 52), copper, stainless steel, titanium, zirconium, NITINOL®, ALUMEL®, KANTHANAL®, CHROMEL®, KOVAR®, combinations or alloys of the same and the like. The material for the heating element 20 can be chosen to provide Resistance Temperature Detector (RTD) functionality, wherein temperature is indirectly measured as a function of impedance. Alloy 52 is considered to be one material suitable for providing RTD functionality to the resistive coil. In various embodiments the resistive coil may be housed in a plastic cover, for example a fluorinated ethylene propylene (FEP) cover.

The heating segment 15 is secured at the distal end 13 of the elongate catheter shaft 12, with, in some embodiments, the catheter shaft 12 and the heating segment 15 together being considered a catheter. The catheter shaft 12 may be used to maneuver the heating element 20 into a desired placement within a HAS. In certain embodiments, the catheter shaft 12 comprises a biocompatible material having a low coefficient of friction. For example, the catheter shaft 12 may comprise polyether ether ketone (PEEK), polyethylene, or polytetrafluoroethylene (PTFE), such as TEFLON®. In other embodiments, the catheter shaft 12 may comprise polyimide, thermoplastic elastomer (TPE), such as HYTREL®, polyether block amide (PEBA), such as PEBAX®, nylon, or any other such suitable material.

In certain embodiments, the catheter shaft 12 is sized to fit within a vascular structure that may be between approximately 1 mm and approximately 25 mm in diameter and, preferably, between approximately 2 mm and approximately 18 mm. The proximal end 14 of the catheter shaft 12 includes a handle 16 that may include a connection for interfacing with the power source 18 through the cable 17, and/or a port for fluid or guidewire passage. The handle 16 may be integrally connected to the cable 17, or the handle 16 may be removably connected to the cable 17.

Figure 1A:
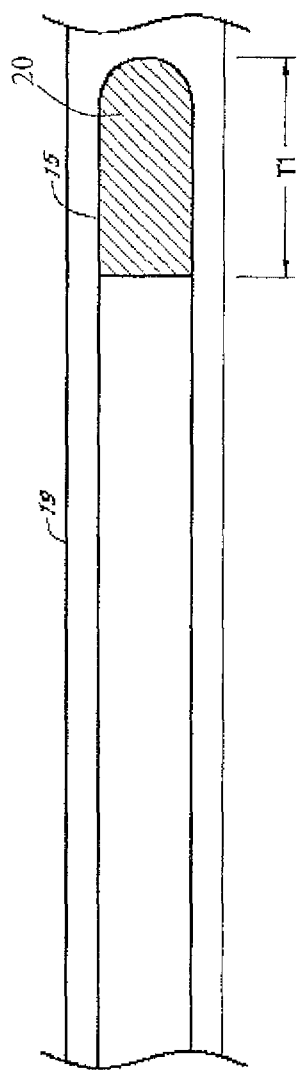
FIGS. 1A and 1B are side elevation views of an example procedure using the medical treatment system of FIG. 1.
Figure 1B:
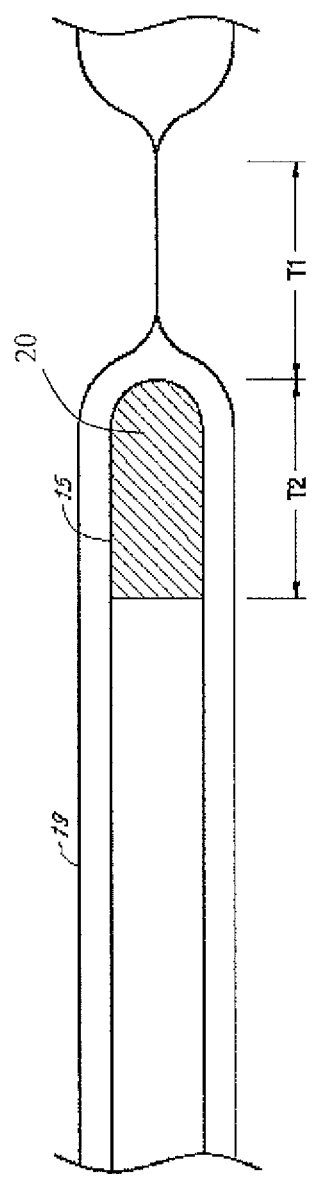

The exemplary medical treatment system 10 may be used in various medical procedures, including endovenous treatments to treat venous reflux. Specifically, referring to FIG. 1A, a method may comprise inserting the heating segment 15 into a distal-most section of a HAS 19 to be treated. The heating segment 15 is then aligned with a first treatment location T1 within the HAS. Power is then applied to the heating segment 15 for a desired length of time to treat the first treatment location T1. After a desired dwell time, such as after the HAS has collapsed as shown in FIG. 1B, the power supplied to the heating segment 15 may be reduced or shut off. With the power off (or substantially reduced), the heating segment 15 may then be moved proximally until the distal end of the heating segment 15 is adjacent to the proximal end of the first treatment location T1, as shown in FIG. 1B. At this second treatment location T2 within the HAS 19, power is again applied to the heating segment 15 for a desired length of time to treat the HAS at the second treatment location T2. This process is repeated until the treatment of the HAS is complete. In some embodiments, T1 and T2 may overlap. While T1 and T2 are shown adjacent to one another in the same HAS, T1 and T2 may be in different locations, such as different HAS.

In certain embodiments, the generator system includes at least one source of direct current (DC) power and modulation circuitry for modulating that power so that RF energy may be applied to the heating segment 15. In most embodiments the RF energy is generated by modulating DC power applied to the heating segment 15, in some embodiments by pulse width modulation (PWM) of the DC power applied to the heating segment 15. The modulation circuitry may be, for example, pulse width modulation circuitry, which in some embodiments comprises pulse width modulation driver circuitry and a switch. In several embodiments the source of DC power is coupled to the heating segment 15 by a switch, with the switch opened and closed for various portions of a periodic cycle in accordance with a pulse width modulation signal. In most embodiments the periodic cycle has a frequency in the radio frequency range, and in some embodiments the periodic cycle has a frequency range between 1 kHz and 50 kHz, inclusive. In most embodiments power is applied to the heating segment 15 when the switch is closed and not applied when the switch is in the open position, but in some embodiments the converse may be true. In some embodiments the switch may be provided, at least in part, by use of switch used for transfer of power, and in some embodiments the switch may include a power MOSFET or an insulated-gate bipolar transistor (IGBT). The generator system 18 in various embodiments incorporates a controller. The controller may be, in various embodiments, one or more processors, FPGAs, CPLDs, DSPs, or some combination thereof. The controller may perform various functions, including determining a duty cycle of the PWM based at least upon readings from a temperature sensor or sensors (e.g., a thermocouple, a thermistor, a resistance temperature device, an optical or infrared sensor, combinations of the same or the like) located in or adjacent to the heating segment 15. For example, the controller may heat the the heating segment 15 to a set temperature. In an alternative embodiment, the user selects a constant power output of the generator system 18. For example, the user may manually adjust the power output relative to the temperature display from a temperature sensor in the heating segment 15.

In some embodiments the generator system 18 includes multiple DC power sources, with different ones of the multiple DC power sources selectable, for example by the controller commanding operation of power switching circuitry, for use in provision of power to the heating element 20. For example, in some embodiments the generator system 18 may include, or be provided power from, a battery as one DC power source and an AC/DC power converter coupled to an AC main (utility or generator power source), with the controller and power switching circuitry selecting use of one power source or the other based on, for example, availability of power from the AC derived power source. In this context, as shown in FIG. 1, an AC/DC power converter 21, coupled to a housing of the generator system 18 by an electrical coupling 23 and coupled to a source of AC power by an electrical coupling 25, may be considered part of the generator system 18. Alternatively, the power converter 21 may be integral to the generator system 18, such as being a part of the internal electronics. In some embodiments the controller and power switching circuitry may switch the source of power while power is generally being provided to the heating element 20, allowing for power source switching during operation of the medical treatment system 10.

Figure 2:
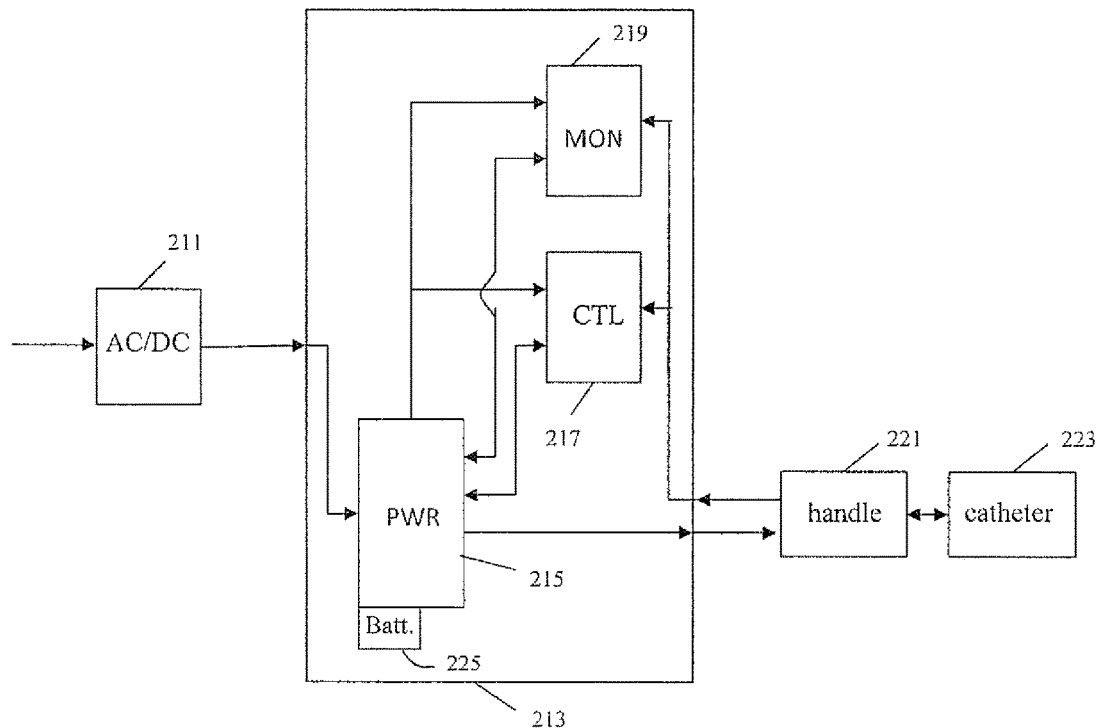
FIG. 2 is a block diagram of an electrosurgical ablation device in accordance with aspects of the invention.

FIG. 2 is a block diagram of an electrosurgical ablation device in accordance with aspects of the invention. In FIG. 2, an AC/DC power converter 211 receives AC power from a power source such as a utility or generator. The AC/DC power converter 211 converts the AC power to DC power. For example, the AC power converter 211 may receive AC power in the range of 100-240 VA, and output power nominally at 24 V DC, with available current for example in the range of a few to several amps.

The DC power is provided, or made available to, a generator unit 213, such as the generator system 18 described above. The generator unit 213 provides power to a heating segment (not shown) in FIG. 2 by way of providing power to a handle 221 and a catheter 223 coupled to the handle 221, with the catheter 223 including the heating segment, for example as discussed with respect to FIG. 1, with reference to heating segment 15, handle 16 and catheter shaft 12. In most embodiments the provided power is pulse width modulated DC power. In many embodiments, and as illustrated in FIG. 2, the generator unit 213 also receives signals from the catheter 223, for example signals indicative of temperature of the heating segment. In such embodiment, the generator unit 213 may adjust a duty cycle of the PWM so as to adjust the temperature of the heating segment to a desired setting. In many embodiments the PWM has a periodic cycle in the RF range, and in some embodiments has a periodic cycle in the range of 1 kHz to 50 kHz, inclusive.

The generator unit 213 includes a power block 215 and, in the embodiment illustrated in FIG. 2, a control block 217 and a monitor block 219.

The power block 215 receives DC power sourced from the AC/DC power converter 211. The power block 215 provides power to the handle 221 and the catheter 223 coupled to the handle 221. The catheter 223 includes a heating segment (not shown), for example as discussed with respect to FIG. 1. The power block 215 therefore effectively provides power to the heating segment. In providing power to the heating segment, the power block 215 modulates DC power to provide modulated RF power to the heating segment, for example using modulation circuitry of the power block 215. In most embodiments the modulation is pulse width modulation (PWM), and the modulation circuitry may be pulse width modulation circuitry, for example including pulse width modulation driver circuitry and a switch. In various embodiments duty cycle of the PWM is determined by the control block 217, for example based on a desired temperature of the heating segment and signals from the catheter 223 indicative of temperature of the heating segment. In some embodiments the DC power which is modulated is at a different voltage than that provided by the AC/DC power converter 211, and in such embodiments one or more DC/DC power converters may be utilized to provide the DC power which is modulated. In some embodiments the AC/DC converter 211 provides DC power at 24 Volts, and the DC power which is modulated is about 15 Volts, for example 15 Volts to 16.8 Volts or 15.5 Volts.

The power block 215 also provides power signals, and in some embodiments status signals, to a control block 217 and the monitor block 219. The power signals provided to the control block 217 and the monitor block 219 are in some embodiments appropriate for powering of circuitry within those blocks, and in other embodiments are appropriate for use by power control circuitry within those other blocks in powering circuitry, for example CMOS circuitry. The status signals may provide various signals relating to the status of power available to the power block 215.

In some embodiments the power block 215 also includes a battery 225 and, in some such embodiments, a battery charger. The battery 225 may be in the form of a battery pack. In various embodiments the battery 225 may be physically separate from the power block 215, and in some embodiments may be external to a housing of the generator unit 213. In some embodiments the battery 225 may be for example a Lithium-ion battery pack. A Lithium-ion battery may be rechargeable, and in embodiments in which rechargeable batteries are used, the power block 215 may include battery charging circuitry. The battery charging circuitry may be provided power from the AC/DC power converter 211 in some embodiments, or a DC/DC power converter as previously discussed.

In embodiments in which the power block 215 includes a battery 225, the power block 215 may select, for example, using power switching circuitry of the power block 215, one or the other of DC power sourced from the AC/DC power converter 211 or DC power sourced from the battery 225 for modulation and provision to the heating segment of the catheter 223. In some embodiments the power block 215 may utilize DC power sourced from the AC/DC power converter 211 if such DC power is available, and utilize DC power sourced from the battery 225 if DC power is not available from the AC/DC power converter 211. Similarly, power signals to the control block 217 and monitor block 219 also may be selected from either the AC/DC power converter 211 or the battery 225. In some embodiments status of availability of power from the AC/DC power converter 211 is provided to the control block 217, and the control block 217 provides command signals to the power block 215 instructing the power block 215 as to which source of power to utilize.

AC/DC power converter 211 is provided to the control block 217, and the control block 217 provides command signals to the power block 215 instructing the power block 217 as to which source of power to utilize.

As indicated above, the control block 217 may receive signals indicative of temperature of the heating segment from the catheter 223 (by way of the handle 221) and signals indicative of availability of power sourced from the AC/DC power converter 211. Based on these signals, and in various embodiments other signals, the control block 217 may determine a duty cycle for pulse width modulation of the DC power to be provided to the catheter 223 and selection of a source of power to provide that DC power. Results of those determinations may be provided to the power block 215 in the form of command signals to the power block 215. In some embodiments the command signals include a signal indicating a duty cycle for PWM of the DC power. In some embodiments the control block 217 includes a programmable processor to make those determinations. The control block 217 may be implemented using a microcontroller and associated circuitry in various embodiments. In some embodiments the control block 217 also includes power regulation circuitry for regulating power provided by the power block 215 for operation of circuitry of the control block 217. In various embodiments the control block 217 also receives signals indicative of user inputs to the generator unit 213, and provides commands for display of indicators, for example LED indicators, of the generator unit 213.

The monitor block 219 also receives signals indicative of temperature about the heating segment from the catheter 223 (by way of the handle 221), as well as power and status signals from the power block 215. The monitor block 219 may include circuitry for performing various monitoring functions related to the status of the generator unit 213 and catheter 223.

Figure 3:
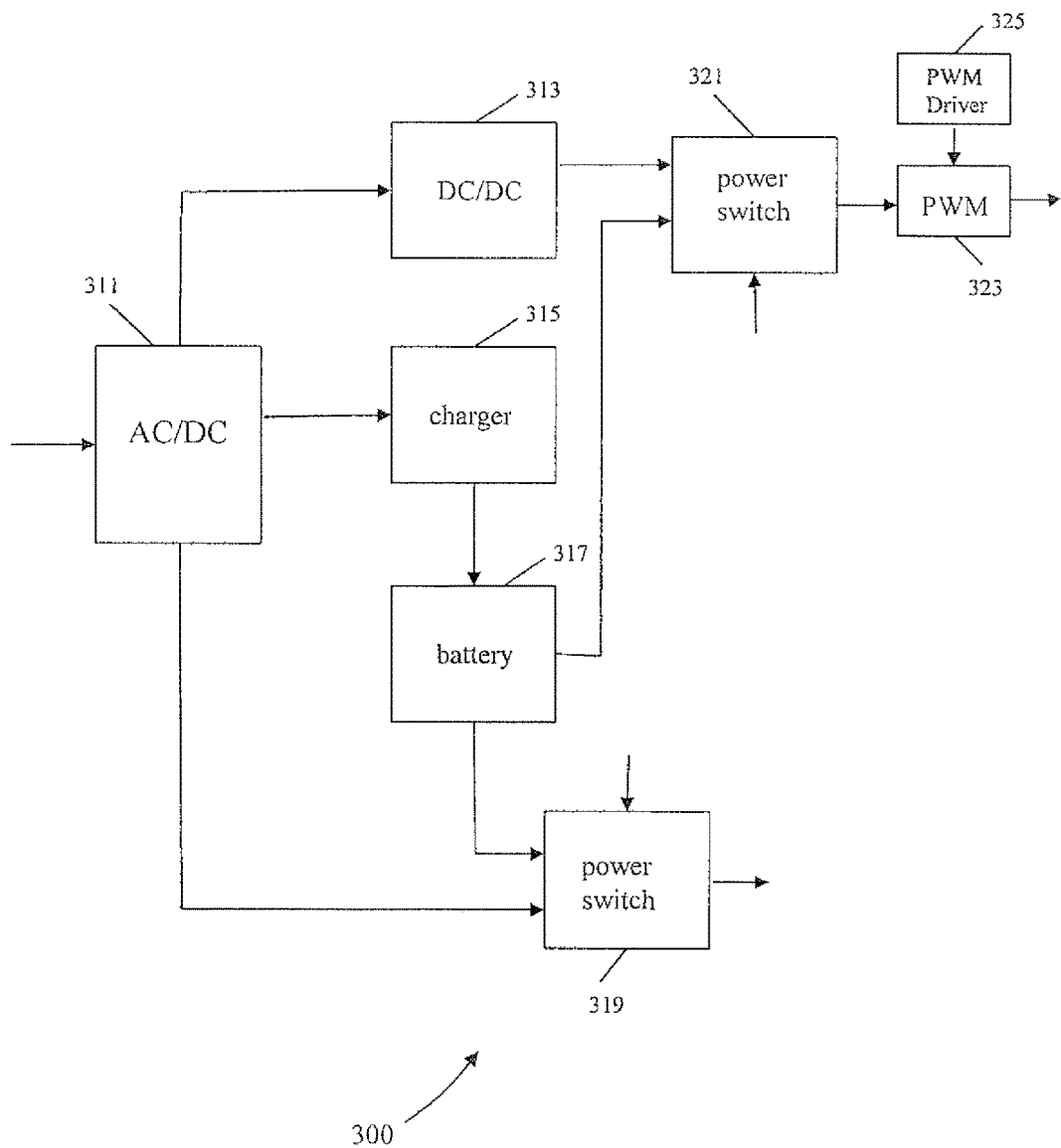
FIG. 3 is a block diagram of a power block of an electrosurgical ablation device in accordance with aspects of the invention.

FIG. 3 is a block diagram of a power block 300 in accordance with aspects of the invention. In some embodiments the power block 300 of FIG. 3 is the power block 215 of FIG. 2, and in some embodiments the power block 300 of FIG. 3 is similar to the power block 215 of FIG. 2. In various embodiments the power block 300 of FIG. 3 is a portion of the power block 215 of FIG. 2, and in some embodiments the power block 300 of FIG. 3 includes circuitry found in other blocks of the system of FIG. 2.

The power block 300 of FIG. 3 includes an AC/DC power converter 311. In various embodiments, however, the AC/DC power converter 311 is external to the power block 300. The AC/DC power converter 311 is coupled to a source of AC power, for example a utility main or a generator, and the AC/DC power converter 311 converts AC power to DC power.

The DC power supplied by the AC/DC power converter 311 is provided to a DC/DC power converter 313. In most embodiments the DC/DC power converter 313 converts the DC power supplied by the AC/DC power converter 311 to a different power level. For example, the AC/DC power converter 311 may provide DC power at 24 Volts DC and the DC/DC power converter 313 may convert the power to 15.5 Volts DC. In some embodiments additional DC/DC power converters may be included between the AC/DC power converter 311 and the DC/DC power converter 313, for example to provide for electrical isolation features in event of voltage spikes from external sources. DC power from the DC/DC power converter 313 is provided to a pulse width modulator 323, for provision of pulse width modulated power to a heating segment of a catheter.

The pulse width modulator 323, which in some embodiments comprises a switch, modulates the DC power to provide modulated DC power for use by a heating segment of a catheter, for example heating segment 15 of FIG. 1. The pulse width modulator 323 modulates the DC power in accordance with signals from a PWM driver 325, and in some embodiments the PWM driver comprises PWM driver circuitry, with the PWM driver circuitry and the switch together comprising PWM modulation circuitry. In some embodiments the PWM driver 325 is external to the power block. The PWM driver 325 provides signals to the pulse width modulator 323 commanding the pulse width modulator 323 to turn on and off output power over various portions of a cycle. In some embodiments the cycle is at a frequency in the range of 1 kHz to 50 kHz, inclusive. In many embodiments the PWM driver 325 provides the signals driving operation of the pulse width modulator 323 based on a command signal, for example provided by a control block, for example the control block 217 of FIG. 2, indicating a desired duty cycle for pulse width modulation.

Figure 4:
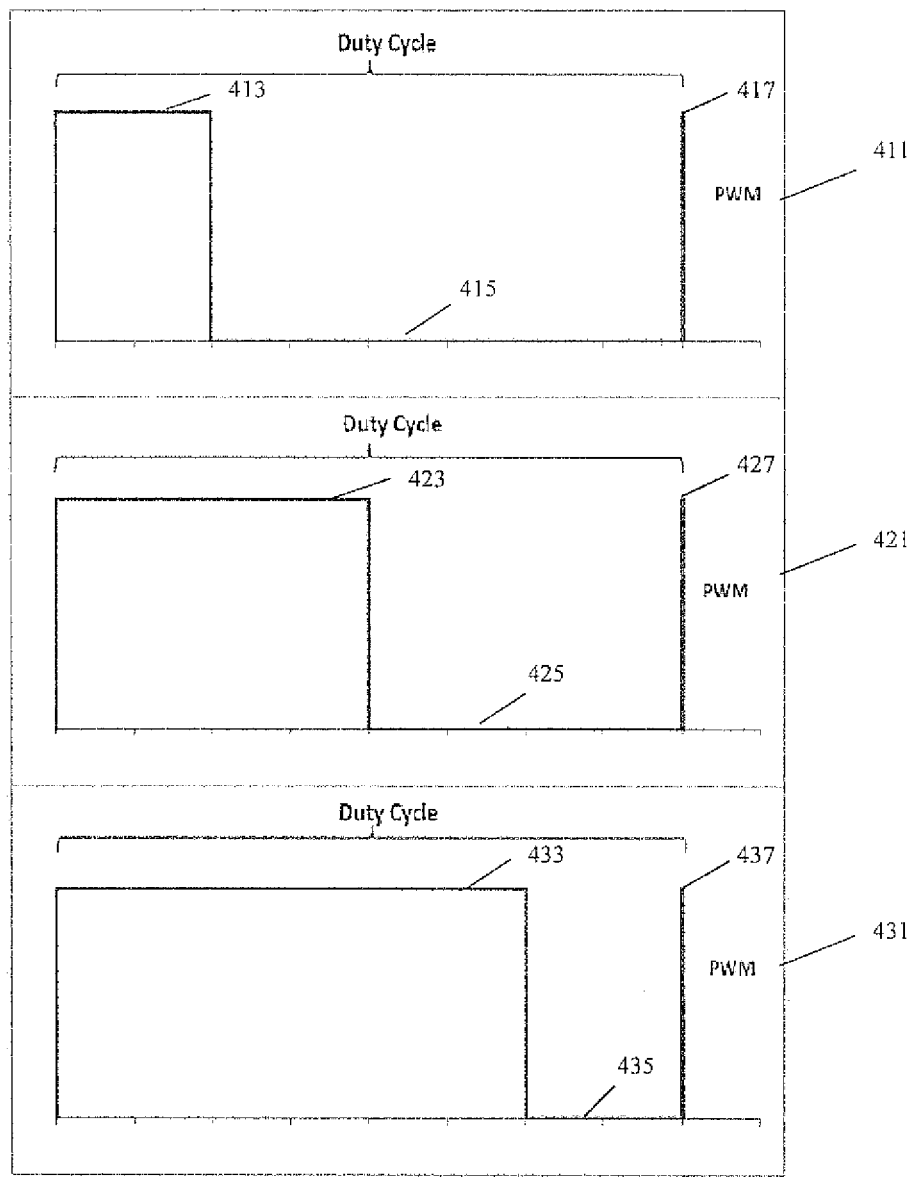
FIG. 4 is a set of charts showing pulse width modulation of DC power in accordance with aspects of the invention.

For illustrative purposes, FIG. 4 includes charts illustrating example on and off portions of a cycle for various duty cycles. In the charts, time is shown along an x-axis and output voltage is shown along a y-axis. The charts show idealized output voltages, as for example in most embodiments rises and falls in output voltage will take place during discrete periods of time. A first chart 411 illustrates a 25% duty cycle, with a high output voltage during a time period 413, a low output voltage during a time period 415, with a return to the high output voltage at an end 417 of the time period 415. The time periods 413 and 415 faun a complete cycle, with the time period 413 being 25% of the cycle and the time period 415 being 75% of the cycle. A second chart 421 illustrates a 50% duty cycle, with a high output voltage during a time period 423, a low output voltage during a time period 425, with a return to the high output voltage at an end 427 of the time period 425. The time periods 423 and 425 form a complete cycle, with the time period 423 and the time period 425 each being 50% of the cycle. A third chart 431 illustrates a 75% duty cycle, with a high output voltage during a time period 433, a low output voltage during a time period 435, with a return to the high output voltage at an end 437 of the time period 435. The time periods 433 and 435 form a complete cycle, with the time period 433 being 75% of the cycle and the time period 435 being 25% of the cycle.

Returning to FIG. 3, in some embodiments, and as illustrated in FIG. 3, either AC sourced power or battery sourced power may be used to provide DC power for modulation. Accordingly, in the embodiment of FIG. 3 the power block 300 includes a battery 317. In various embodiments, the battery 317 may be separate from the power block 300. The battery 317 also may provide DC power to the pulse width modulator 323, with a first power switch 321 selectably choosing either the AC sourced power provided by the DC/DC converter 313 or DC power for modulation by the pulse width modulator 323. In some embodiments the first power switch 321 selects the AC sourced power or the battery power based on a control signal provided by a control block, for example control block 217 as discussed with respect to FIG. 2. In some embodiments the first power switch 321 is not used, with an output of the battery 317 and an output of the DC/DC power converter 313 connected in parallel, with both the DC/DC power converter 313 output and the battery 317 output presenting a high impedance.

In embodiments with a battery 317, the power block 300 may also include a battery charger module 315. As with the battery 317 in various embodiments, the battery charger module 315 may be external to the power block. The battery charger module 315 includes battery charging circuitry for charging the battery 317 using power from the AC/DC converter 311.

As shown in FIG. 3, the AC/DC power converter 311 and the battery 317 are also coupled to a second power switch 319. The second power switch 319 provides power for use by various circuit elements, for example circuitry of the control block 217 and monitor block 219 of the generator unit 213 of FIG. 2.

Figure 5:
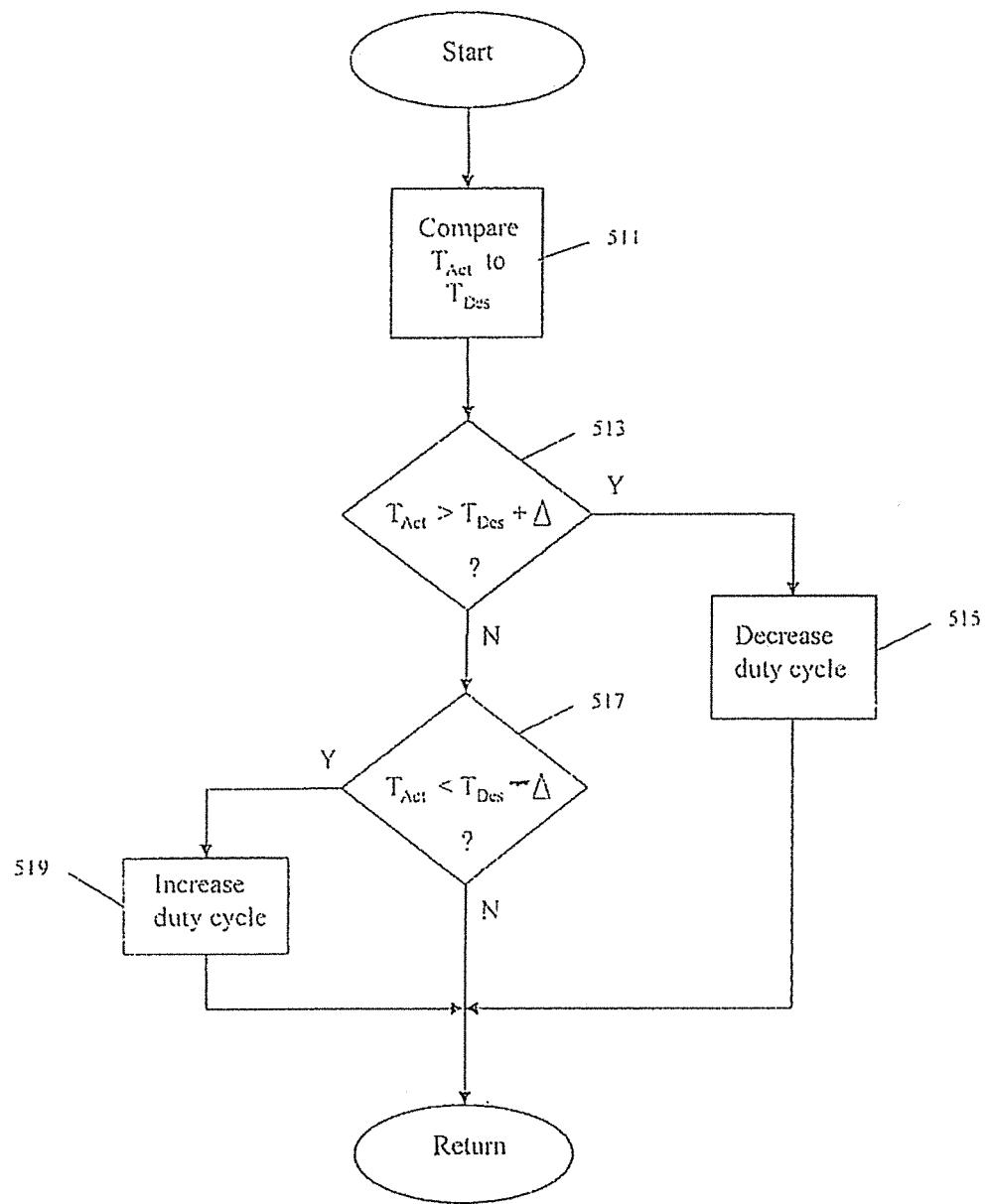
FIG. 5 is flow diagram of a process for determining adjustments to a duty cycle in accordance with aspects of the invention.

FIG. 5 is a flow diagram of a process for determining adjustments to a duty cycle in accordance with aspects of the invention. In some embodiments the process is performed by circuitry, which may be in the form of a processor. In some embodiments the process is performed by the control block 217 of FIG. 2, and in some embodiments the process is performed by a programmable processor of the control block 217 of FIG. 2.

In block 511 the process compares actual temperature of a heating segment of a catheter, or temperature about a heating segment of a catheter, with a desired temperature. The temperature about the heating segment of the catheter may be provided by a temperature sensor located in the catheter near the heating segment, for example. The desired temperature may be a constant temperature in some embodiments. In some embodiments the desired temperature may be enterable by a user into, for example, the generator unit 213 of FIG. 2, with an entered temperature received by the control block 217 of FIG. 2.

In block 513 the process determines if the actual temperature is greater than the desired temperature plus a first offset value. The use of an offset value, which may be programmable in various embodiments, may be useful in avoiding, for example, excessive frequency of changes in the duty cycle, while generally maintaining the actual temperature in a desired temperature band. If the actual temperature is greater than the desired temperature plus the offset value, the process continues to block 515, otherwise the process continues to block 517.

In block 515 the process decreases the duty cycle. In some embodiments the process decreases the duty cycle by a set amount, down to a minimum, which is greater than 0% in some embodiments. The process thereafter returns.

In block 517 the process determines if the actual temperature is less than the desired temperature minus a second offset value. The second offset value is in some embodiments the same as the first offset value. In some embodiments the second offset value is greater than the first offset value, and in some embodiments the second offset value is less than the first offset value. If the actual temperature is less than the desired temperature minus the offset value, the process continues to block 519, otherwise the process returns.

In block 519 the process increases the duty cycle. In some embodiments the process increases the duty cycle by a set amount, up to a maximum, which is less than 100% in some embodiments. The process thereafter returns.

Figure 6:
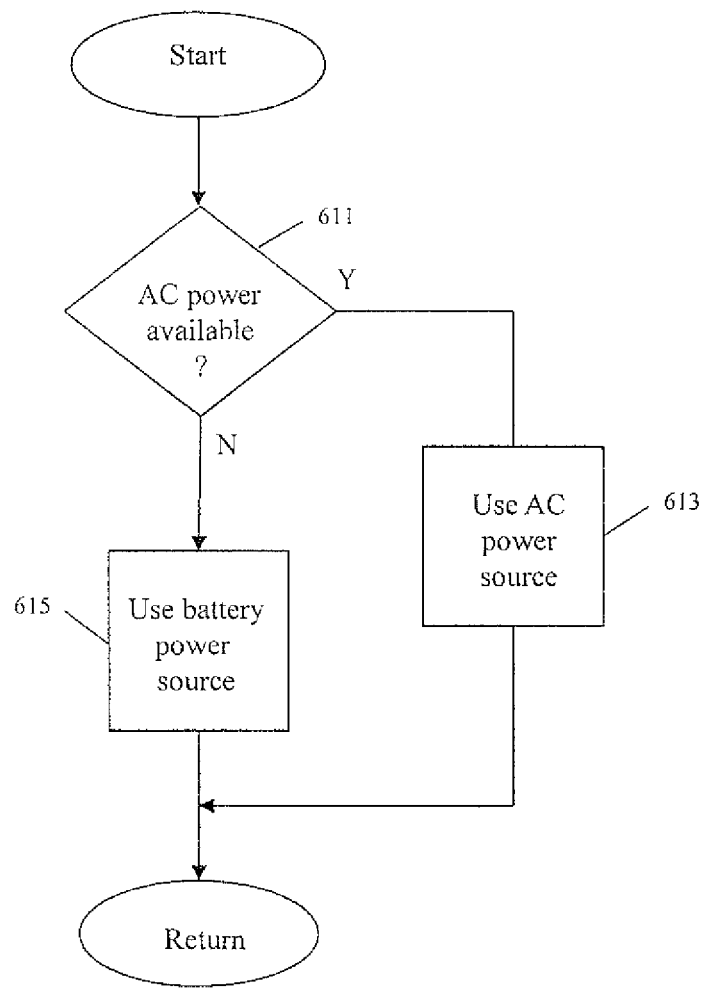
FIG. 6 is a flow diagram of a process for determining whether to use AC sourced power or battery sourced power in accordance with aspects of the invention

FIG. 6 is a flow diagram of a process for determining whether to use AC sourced power or battery sourced power in accordance with aspects of the invention. In some embodiments the process is performed by circuitry, which may be in the form of a processor. In some embodiments the process is performed by the control block 217 of FIG. 2, and in some embodiments the process is performed by a programmable processor of the control block 217 of FIG. 2. In some embodiments the process is performed before power is applied to a heating segment of a catheter. In some embodiments the process is performed while power is applied to the heating segment. In some embodiments the process is performed both before power is applied to the heating segment and while power is applied to the heating segment.

In block 611 the process determines if AC sourced power is available. The process may determine whether AC sourced power is available based on a signal provided by, for example, the power block 215 of the generator unit 213 of FIG. 2. If AC sourced power is available the process continues to block 613, otherwise the process continues to block 615.

In block 613 the process uses AC sourced power to supply DC power to be modulated for provision to the heating segment of the catheter. In various embodiments the process also utilizes AC sourced power, with generally the AC sourced power converted to DC by for example an AC/DC power converter, for powering of circuitry and, in some embodiments, for charging of the battery. The process thereafter returns.

In block 615 the process uses battery sourced power to supply DC power to be modulated for provision to the heating segment of the catheter. In various embodiments the process also utilizes the battery sourced power for powering of circuitry, and in some embodiments commands ceasing of charging of the battery. The process thereafter returns.

Although the invention has been discussed with respect to various embodiments, it should be recognized that the invention comprises the novel and non-obvious claims supported by this disclosure.

What is claimed is:

1. A direct current (DC) powered electrosurgical ablation device, the device comprising:
   a catheter including a heating segment configured to ablate tissue;
   modulation circuitry configured to modulate DC power using pulse width modulation (PWM) having a duty cycle selected to only be greater than a minimum duty cycle of 0% and less than a maximum duty cycle of 100% to provide modulated DC power pulses directly to the heating segment; and
   at least one DC power source configured to provide the DC power to the modulation circuitry.

2. The device of claim 1, wherein the modulation circuitry includes pulse width modulation (PWM) driver circuitry and a switch.

3. The device of claim 1, wherein the at least one DC power source comprises two DC power sources.

4. The device of claim 3 wherein a first of the two DC power sources comprises an AC/DC power converter and a second of the two DC power sources comprises a battery.

5. The device of claim 4, further comprising a switch to switchably provide power from either the AC/DC power converter or the battery to the modulation circuitry for provision to the heating segment.

6. The device of claim 4, wherein the AC/DC power converter and the battery are coupled in parallel to the modulation circuitry.

7. The device of claim 4, further comprising a DC/DC power converter coupled between the AC/DC power converter and the modulation circuitry.

8. The device of claim 1, wherein the heating segment comprises a resistive coil.

9. The device of claim 8, wherein the resistive coil is housed in a plastic cover.

10. The device of claim 1, wherein a frequency of a periodic cycle of the PWM is in a range of 1 kHz to 50 kHz, inclusive.

11. A method of operating an electrosurgical ablation device, the method comprising:
    providing direct current (DC) power;
    modulating the DC power using pulse width modulation (PWM) having a duty cycle selected to only be greater than a minimum duty cycle of 0% and less than a maximum duty cycle of 100% to produce modulated DC power pulses; and
    applying the modulated DC power pulses directly to a heating element in a catheter to ablate tissue with the heating element.

12. The method of claim 11, wherein modulating the DC power using PWM comprises providing the DC power to a switch, and opening and closing the switch using a PWM driver signal.

13. The method of claim 11, wherein a frequency of a periodic cycle of the PWM is in the range of 1 kHz to 50 kHz, inclusive.

14. The method of claim 11, wherein providing the DC power comprises selectably providing the DC power from an AC/DC power converter or from a battery.

15. The method of claim 14, wherein selectably providing the DC power from the AC/DC power converter or from the battery is based on availability of AC power to the AC/DC power converter.

16. The method of claim 15, wherein selectably providing the DC power from the AC/DC power converter or from the battery may be performed during application of the modulated DC power pulses to the heating element.

17. A method comprising:
providing, by an electrosurgical ablation device, direct current (DC) power;
modulating the DC power using pulse width modulation (PWM) having a duty cycle selected to only be greater than a minimum duty cycle of 0% and less than a maximum duty cycle of 100% to produce modulated DC power pulses;
applying the modulated DC power pulses directly to a heating element in a catheter; and
ablating, with the heating element in the catheter, tissue of a patient while the modulated DC power pulses are applied to the heating element,
wherein providing the DC power comprises selectably providing the DC power from an AC/DC power converter or from a battery.

18. The method of claim 17, wherein selectably providing the DC power from the battery occurs when power is unavailable from the AC/DC power converter.

19. The method of claim 17, wherein modulating the DC power using PWM comprises providing the DC power to a switch, and opening and closing the switch using a PWM driver signal.

20. The method of 17, wherein selectably providing the DC power from the AC/DC power converter or from the battery is performed during application of the modulated DC power pulses to the heating element from the AC/DC power converter or from the battery.

21. A method of operating an electrosurgical ablation device, the method comprising:
providing direct current (DC) power, wherein providing the DC power comprises selectably providing the DC power from an AC/DC power converter or from a battery based on availability of AC power to the AC/DC power converter;
modulating the DC power using pulse width modulation (PWM) having a duty cycle selected to only be greater than a minimum duty cycle of 0% and less than a maximum duty cycle of 100% to produce modulated DC power pulses, wherein modulating the DC power using PWM comprises providing the DC power to a switch, and opening and closing the switch using a PWM driver signal; and
applying the modulated DC power pulses directly to a heating element in a catheter to ablate tissue with the heating element,
wherein selectably providing the DC power from the AC/DC power converter or from the battery is performed during application of the modulated DC power pulses directly to the heating element from the AC/DC power converter or from the battery.

22. The method of claim 21, wherein a frequency of a periodic cycle of the PWM is in the range of 1 kHz to 50 kHz, inclusive.

23. The method of claim 11, further comprising:
determining a first temperature of the heating element of the catheter;
comparing the first temperature to a desired temperature plus an offset value; and
responsive to determining that the first temperature is greater than the desired temperature plus the offset value, decreasing a duty cycle of the PWM between the minimum duty cycle and the maximum duty cycle.

24. The method of claim 11, further comprising:
determining a first temperature of the heating element of the catheter;
comparing the first temperature to a desired temperature minus an offset value; and
responsive to determining that the first temperature is less than the desired temperature minus the offset value, increasing a duty cycle of the PWM between the minimum duty cycle and the maximum duty cycle.

* * * * *